(12) United States Patent
Brunel

(10) Patent No.: US 8,670,120 B2
(45) Date of Patent: Mar. 11, 2014

(54) DEVICE FOR ANALYZING A POLYPHASE MIXTURE VIA A LIGHT BEAM BACKSCATTERED BY SAID MIXTURE

(75) Inventor: Laurent Brunel, Peyrins (FR)

(73) Assignee: Formulaction, l'Union (FR)

( * ) Notice: Subject to any disclaimer, the term of this patent is extended or adjusted under 35 U.S.C. 154(b) by 316 days.

(21) Appl. No.: 13/131,046

(22) PCT Filed: Nov. 26, 2009

(86) PCT No.: PCT/FR2009/052303
§ 371 (c)(1),
(2), (4) Date: May 25, 2011

(87) PCT Pub. No.: WO2010/061137
PCT Pub. Date: Jun. 3, 2010

(65) Prior Publication Data
US 2011/0228272 A1    Sep. 22, 2011

(30) Foreign Application Priority Data
Nov. 26, 2008  (FR) ...................................... 08 58030

(51) Int. Cl.
    G01N 21/00    (2006.01)
(52) U.S. Cl.
    USPC ......................................................... 356/342
(58) Field of Classification Search
    None
    See application file for complete search history.

(56) References Cited

U.S. PATENT DOCUMENTS

| 4,028,553 | A |   | 6/1977  | Farcinade |
| 5,523,560 | A |   | 6/1996  | Manique et al. |
| 5,619,043 | A | * | 4/1997  | Preikschat et al. ............ 250/574 |
| 5,783,826 | A | * | 7/1998  | Meunier .................... 250/341.8 |
| 6,091,492 | A | * | 7/2000  | Strickland et al. ............ 356/336 |
| 6,466,319 | B2 | * | 10/2002 | Harris et al. ................. 356/338 |
| 6,765,656 | B2 | * | 7/2004  | Johnson ......................... 356/73 |
| 7,268,874 | B2 | * | 9/2007  | Brogioli et al. ............... 356/336 |
| 7,643,134 | B2 | * | 1/2010  | Berndt ............................ 356/39 |
| 7,782,458 | B2 | * | 8/2010  | Snabre et al. ................. 356/336 |

(Continued)

FOREIGN PATENT DOCUMENTS

| EP | 1 241 467 A2 | 9/2002 |
| FR | 2 841 983 A1 | 1/2004 |

(Continued)

*Primary Examiner* — Gordon J Stock, Jr.
(74) *Attorney, Agent, or Firm* — Birch, Stewart, Kolasch & Birch, LLP

(57) ABSTRACT

Device for analyzing a polyphase mixture via a light beam backscattered by said mixture, comprising: a vertical cell capable of containing the polyphase mixture; means for emitting a light beam in the direction of the cell, in such a way that the light beam lies in a vertical plane (PV) covering at least the height (hc) of the cell containing the polyphase mixture; means for receiving a light beam backscattered by the polyphase mixture, covering the height of the backscattered light beam, extending over the height (hc) of the cell containing the polyphase mixture; optical conjugation means placed between the cell and the means for receiving the backscattered beam, the receiving means comprising a matrix center forming a surface for receiving the backscattered beam, lying in vertical and horizontal directions; and means for analyzing the backscattered beam received by the matrix sensor, the light beam emitted in the direction of the cell, adopting, at its interface between the internal surface of the wall of the cell and the polyphase mixture, the form of a vertical line the width of which is shorter, preferably very much shorter, than the free transport path of the polyphase mixture.

20 Claims, 8 Drawing Sheets

(56) References Cited

U.S. PATENT DOCUMENTS

| | | | |
|---|---|---|---|
| 8,149,418 B2 * | 4/2012 | Tearney et al. | 356/479 |
| 8,368,747 B2 * | 2/2013 | Brinz et al. | 348/67 |
| 2002/0147563 A1 * | 10/2002 | Lerche et al. | 702/127 |
| 2006/0061766 A1 | 3/2006 | Brunel | |
| 2010/0007891 A1 * | 1/2010 | Carroll et al. | 356/440 |

FOREIGN PATENT DOCUMENTS

| | | |
|---|---|---|
| GB | 2 420 403 A | 5/2006 |
| WO | WO 2005/001449 A1 | 1/2005 |
| WO | WO 2006/023470 A1 | 3/2006 |
| WO | WO 2008/092535 A1 | 8/2008 |

* cited by examiner

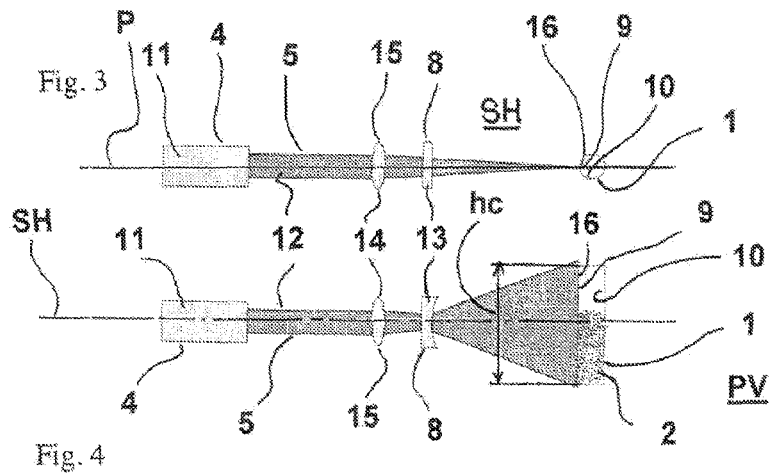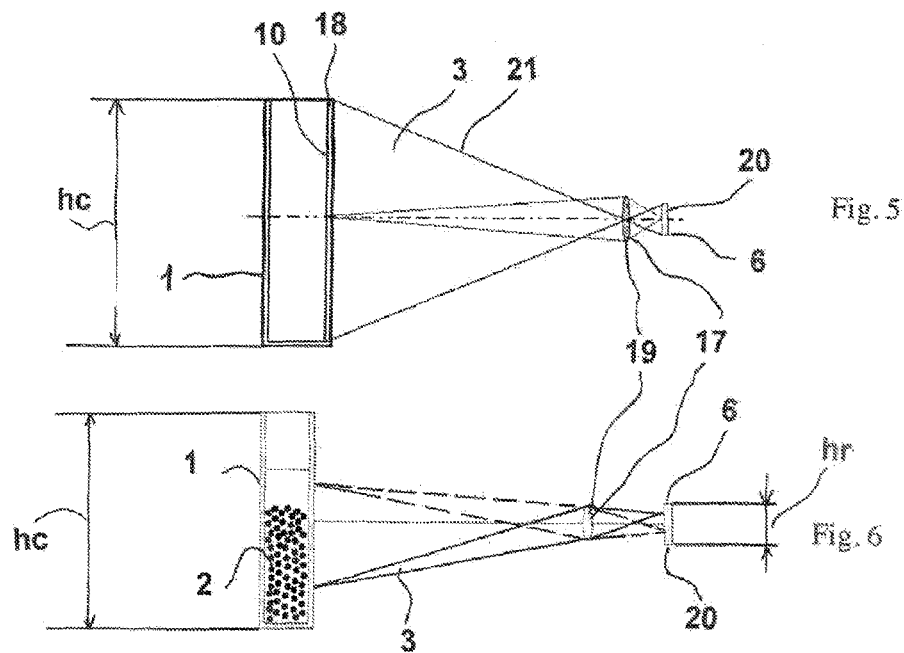

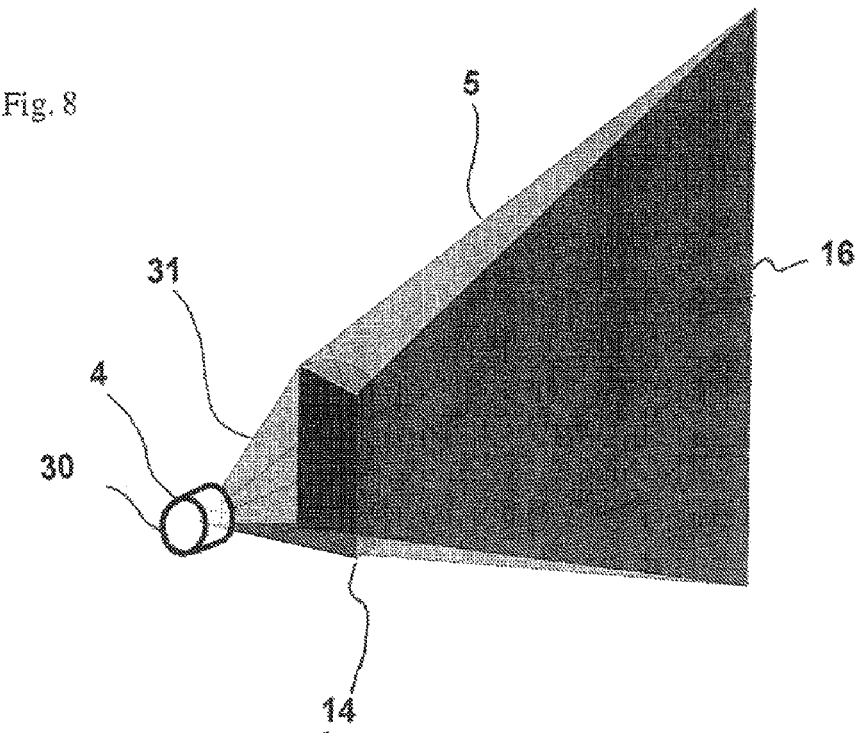

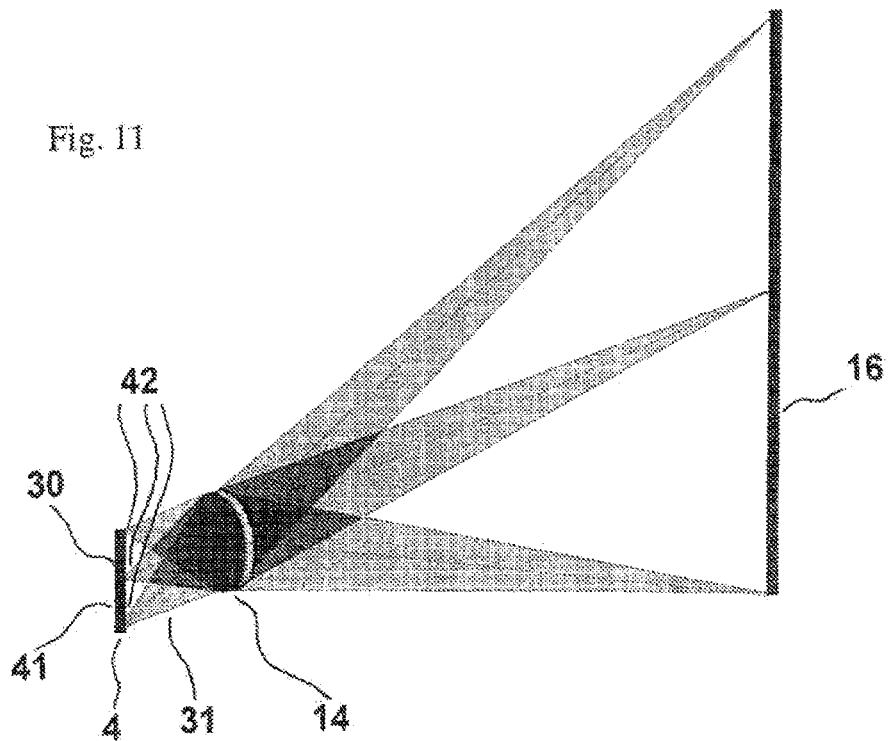
Fig. 11
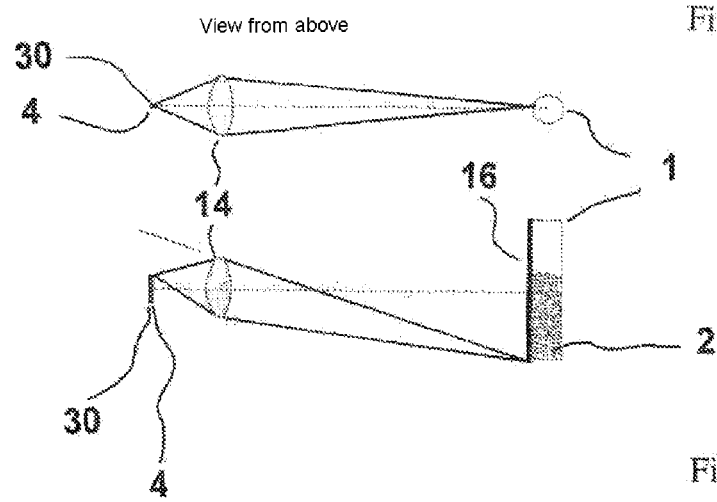
Fig. 12
Fig. 13

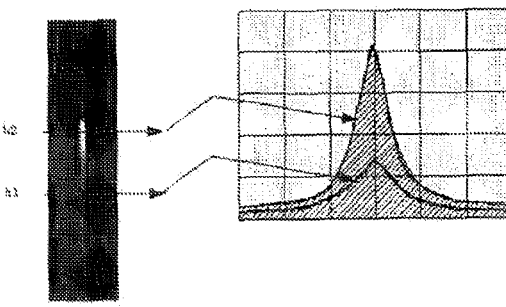
Fig. 14
Fig. 15
Fig. 16
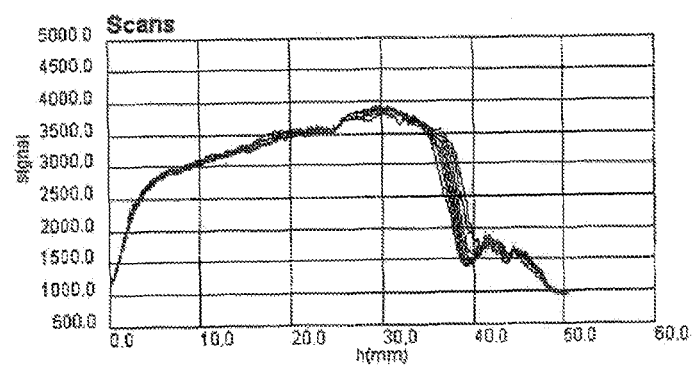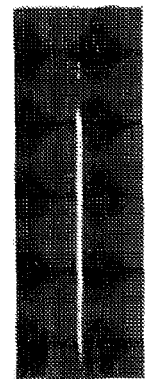
Fig. 17

DEVICE FOR ANALYZING A POLYPHASE MIXTURE VIA A LIGHT BEAM BACKSCATTERED BY SAID MIXTURE

BACKGROUND

1. Field of the Invention

The present invention relates to a device for analyzing a polyphase mixture via a light beam backscattered by said mixture. The device may include:
- a cell having a capacity component of vertical extent, capable of containing the polyphase mixture,
- means for emitting a light beam in the direction of the cell, so that the light beam extends in a vertical plane covering at least a height of the cell capable of containing the polyphase mixture,
- means for receiving the light beam backscattered by said polyphase mixture, covering a backscattered light beam height extending over the height of the cell capable of containing the polyphase mixture.

2. Description of Related Art

Such a device is known for example from the document US 2002/0147563. The measurement of the backscattered light beam with the device according to this document is not satisfactory. This is because any distance of the cell from the backscattering receiver means leads to a great loss of spatial resolution of the measurement.

The document EP 1 241 467 is furthermore known, which relates to an apparatus for inspection and to a system for inspection of foreign matter in containers filled with a liquid. The monitoring device described in this document comprises in particular a light source which sends irradiation light to the transparent container, a means for taking images of the irregular reflection light reflected by the foreign matter contained in the liquid, and an image processing means detecting foreign matter in the liquid.

The document WO 2008/092537 is furthermore known, which relates to an optical characterization device in which a sample is arranged in a light-transparent receptacle, a camera being provided in order to detect the sample. A first light source is arranged so that the sample is lit through in a direction counter to the line of view of the camera. A second light source is arranged on the same side as the camera, and a laser source is arranged transversely to the line of view of the camera.

The document FR 2 841 983 in the name of the Applicant is also known, which relates to a method and a device for measuring a light flux backscattered by a disperse medium, not perturbed by the reflections at the interfaces; the device makes it possible to measure a light flux backscattered by a disperse medium placed on a first side of the wall, by interaction with a plurality of light rays emitted on the second side of the wall, opposite the first side where the disperse medium is placed, and in the direction of said medium, the plurality of light rays being capable of passing through the wall and being at least partially backscattered by the disperse medium in the direction of reception means placed on the second side of the wall, said wall being capable of being passed through by the emitted and backscattered light rays, and of being in contact with the disperse medium. The device comprises:
- means for emitting, toward the wall, light radiation capable of passing through this wall and reaching the disperse medium, so that the latter can in turn emit a plurality of backscattered light rays through the wall with a view to forming a backscattering spot in which at least one central disk-shaped region is defined, the center of which corresponds to the light centroid of the backscattering spot and the radius of which is equal to four times the maximum free transport path $l^*_{max}$ of the disperse medium, the backscattering spot being capable of being imaged at least in part on the reception means,
- means for receiving the light radiation backscattered by the disperse medium through the wall and intended to form the backscattering spot, these reception means covering at least a direction extending from the light centroid of said spot,
- means for suppressing, from the light rays backscattered by the disperse medium, the light rays which come from the central region and have experienced total reflection on the surface forming the interface of the wall with the second side,
- means for measuring spatial sampling of the profile of the light flux received by at least a part of the reception means.

BRIEF SUMMARY OF THE INVENTION

It is an object of the present invention to overcome this drawback and furthermore provide other advantages. More precisely, a device is described for analyzing a polyphase mixture via a light beam backscattered by said mixture, comprising:
- a cell having a capacity component of vertical extent, capable of containing the polyphase mixture,
- means for emitting a light beam in the direction of the cell, so that the light beam extends in a vertical plane covering at least a height of the cell containing the polyphase mixture,
- means for receiving at least a part of the light beam backscattered by said polyphase mixture, covering a backscattered light beam height extending over the height of the cell containing the polyphase mixture, characterized in that it furthermore comprises:
- optical conjugation means arranged between the cell and the means for receiving at least a part of the light beam backscattered by the polyphase mixture,
- said receiver means comprising a matrix sensor provided with a plurality of pixels or the like, forming a surface extending along a vertical direction and a horizontal direction,
- means for analyzing said at least part of the light beam backscattered by the polyphase mixture and received by the matrix sensor via the optical conjugation means,
- the light beam emitted in the direction of the cell having, at its interface between the inner surface of the wall of the cell and the polyphase mixture, a vertical line shape whose width is less, preferably very much less, than the free transport path $l^*$ of the polyphase mixture.

By virtue of the optical conjugation means, the device according to the invention allows high-performance exploitation of the signal transmitted by the backscattered light beam, in combination with the means for analyzing the backscattered beam via the optical conjugation means. The optical conjugation means make it possible in particular to capture a part of the light beam backscattered by a point of the polyphase mixture and to transmit this beam part onto a point of the receiver means; a determined point of the receiver means, for example one or more pixels or the like, is thus made to correspond with a determined point of the mixture, this one-to-one correspondence optimizing the exploitation of the light signal transmitted by the point of the mixture which backscatters the light, by separating it from the neighboring points of the mixture which backscatter the light. The optical conjugation means, combined with the vertical line shape of the light beam of specific thickness as defined, make it possible to obtain an analysis profile of the mixture over the analyzed height, which genuinely depends on the scattering properties of the mixture and not on the vertical line of light.

According to an advantageous characteristic, the optical conjugation means comprise means for collecting and focusing said at least part of the backscattered light beam, of the biconvex lens type.

This characteristic permits a one-to-one relation advantageously implemented between points of the polyphase mixture which extend over the cell height illuminated by the light beam, which itself extends in a vertical plane, and which backscatter the light, and points of the receiver means, for example pixels of a matrix sensor or the like, which is defined by a camera.

According to an advantageous characteristic, the optical conjugation means, arranged between the cell and the means for receiving the light beam backscattered by the polyphase mixture, are arranged so that the height of the receiver means is less than the height of the cell capable of containing said polyphase mixture.

This characteristic makes it possible to reduce the size of the receiver means, and more particularly the size of the matrix sensor or the like, and therefore to reduce the cost of the device while benefiting from analysis over the entire height of the cell. The corresponding arrangement is advantageously obtained by an appropriate form and arrangement of the optical conjugation means between the cell and the matrix sensor or the like, so as to select an appropriate optical magnification generated by the optical conjugation means according to requirements.

According to an advantageous characteristic, the device according to the invention furthermore comprises means for focusing the light beam emitted in the direction of the cell, taken in a horizontal cross section, at its interface between the inner surface of the wall of the cell and the polyphase mixture.

This characteristic makes it possible to obtain an extreme thinness of the light beam striking the cell-mixture interface, thus offering a very high analysis resolution.

According to an advantageous characteristic, the device according to the invention furthermore comprises means for extending the light beam emitted in the direction of the cell, in order to extend said beam in a vertical plane covering at least the height of the cell capable of containing said polyphase mixture, so that the light beam is divergent in said vertical plane at its interface between the inner surface of the wall of the cell and the polyphase mixture.

Projecting a divergent beam onto the measurement cell makes it possible to adapt the measurement height to the height of the mixture to be analyzed in the cell, and more generally the height of the light beam striking the cell to the height of the cell, by modifying the divergence angle of the beam or the distance between the means generating the divergent light beam and the cell, so as to make the height of the mixture analyzed correspond to the height of the beam striking the cell at the mixture-cell interface. An analysis device is thus provided which can be used more flexibly than the prior art device described above in which the rays of the incident light beam, which strike the cell and are intended to be used for the analysis, have to be parallel, because for example it makes it possible to change the cell easily. Furthermore, the divergent incident beam makes it possible to use emitter means which are smaller than the height of the cell and also makes it possible to avoid using focusing means which are excessively large and therefore expensive.

According to an advantageous characteristic, said means for emitting the light beam in the direction of the cell comprise:
  means for generating a light beam, all the light rays of which are mutually parallel,
  said means for extending the light beam emitted in the direction of the cell being interposed between said means for generating a collimated light beam and the cell.

This characteristic makes it possible to use a light generating source which is less elaborate than that which is currently found. The term "collimated" is intended here to mean a light beam whose light rays are parallel.

According to an advantageous characteristic, said means for extending the light beam emitted in the direction of the cell comprise vertically divergent concave cylindrical lens means.

According to an advantageous characteristic, said focusing means are arranged between the means for generating the beam of collimated light and the means for extending the light beam in the vertical plane.

According to an advantageous characteristic, said means for emitting the light beam in the direction of the cell comprise means for generating at least one divergent light beam.

According to an advantageous characteristic, said focusing means comprise convergent lens means.

According to an advantageous characteristic, said focusing means comprise horizontally convergent cylindrical lens means.

According to an advantageous characteristic, said means for generating at least one divergent light beam comprise a linear light source.

According to an advantageous characteristic, said linear light source comprises a plurality of divergent point light sources.

According to an advantageous characteristic, the cell capable of containing said polyphase mixture has a vertical right cylindrical shape.

According to an advantageous characteristic, the cell of vertical right cylindrical shape has a circular cross section.

BRIEF DESCRIPTION OF THE DRAWINGS

Other characteristics will become apparent from the subsequent reading of several exemplary embodiments of the invention, accompanied by the appended drawings, which examples are given by way of nonlimiting illustration.

FIG. 3 represents a view from above of the example in FIG. 2.

FIG. 4 represents a side view of the example in FIG. 2.

FIG. 5 represents a partial schematic side view of the example in FIG. 1, relating to the means for receiving the backscattered light beam.

FIG. 6 represents a similar view to FIG. 5, showing a detail of the backscattered light beam.

FIG. 8 represents a schematic perspective view of a third exemplary embodiment of a device according to the invention, which is partial and concerns the means for emitting a light beam in the direction of the cell.

FIG. 9 represents a view from above of the example in FIG. 8.

FIG. 10 represents a side view of the example in FIG. 8.

FIG. 11 represents a schematic perspective view of a fourth exemplary embodiment of a device according to the invention, which is partial and concerns the means for emitting a light beam in the direction of the cell.

FIG. 12 represents a view from above of the example in FIG. 11.

FIG. 13 represents a side view of the example in FIG. 11.

FIG. 14 represents a view of the backscattering image obtained on the receiver matrix sensor, for an arbitrary mixture.

FIG. 15 represents an example of processing of the image according to FIG. 14.

FIGS. 16 to 18 relate to a first example of use of a device according to the invention, for studying sedimentation.

DETAILED DESCRIPTION

Figure 1:
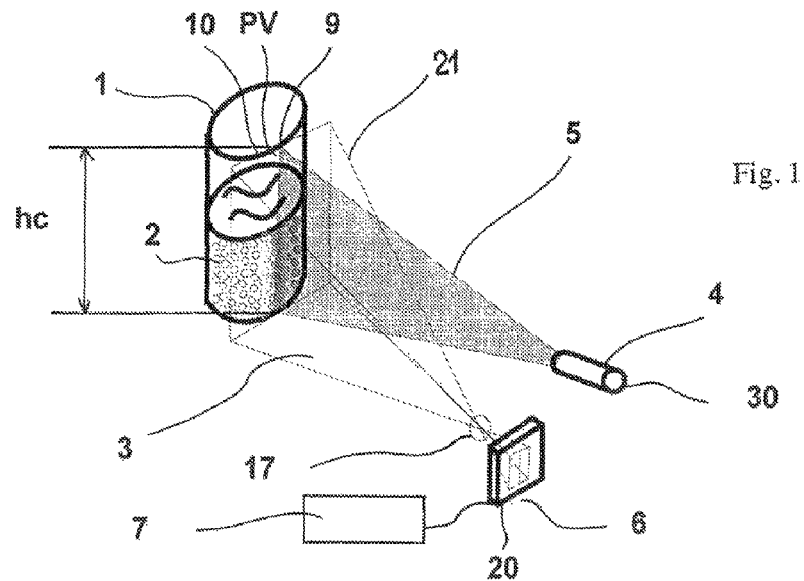
FIG. 1 represents a schematic perspective view of a first exemplary embodiment of a device according to the invention for analyzing a polyphase mixture by means of a light beam backscattered by said mixture.

The device for analyzing a polyphase mixture 2 via a light beam 3 backscattered by said mixture, represented schematically in FIG. 1 comprises:
- a cell 1 having a capacity component of vertical extent, capable of containing the polyphase mixture 2,
- means 4 for emitting a light beam 5 in the direction of the cell 1, so that the light beam 5 extends in a vertical plane PV covering at least a height hc of the cell 1 containing the polyphase mixture 2,
- means 6 for receiving at least a part of the light beam 3 backscattered by the polyphase mixture 2, covering a backscattered light beam 3 height extending over the height hc of the cell 1 containing the polyphase mixture 2,
- optical conjugation means 17 arranged between the cell 1 and the means 6 for receiving at least a part of the light beam 3 backscattered by the polyphase mixture 2,
- the receiver means 6 comprising a matrix sensor 20 provided with a plurality of pixels or the like, forming a surface for receiving the part of the backscattered light beam 3 passing through the optical conjugation means 17, extending along a vertical direction and a horizontal direction,
- means 7 for analyzing the part of the light beam 3 backscattered by the polyphase mixture 2 and received by the matrix sensor 20 via the optical conjugation means 17.

The polyphase mixture 2 analyzed may be of any type, for example a polyphase mixture for which it is desired to analyze the phases, in particular the detection and measurement of phenomena, for example nascent phenomena, of demixing or sedimentation in mixtures as a function of time, for example of emulsions or suspensions. The fields of application of the analysis device according to the invention comprise in particular the chemical and parachemical industry, and more generally all fields for which it is necessary to analyze the structure as well as the stability of a polyphase mixture or ascertain the structure of a mixture or more generally a scattering medium.

The cell 1 having a capacity component of vertical extent, capable of containing the polyphase mixture 2, may for example be a cell having a vertical right cylindrical shape, for example having a circular cross section as represented in FIG. 1. Other shapes of cell and/or cross sections may be suitable, for example having a polygonal, in particular square, cross section, so long as they have a capacity comprising a vertical extent along which gravity can exert its effects, preferably comprising at least one vertical straight wall part illuminated by the light beam 5.

The device preferably comprises a rigid support (not shown) intended to be placed on a surface which is fixed with respect to gravity which makes it possible to place and hold:
- the cell 1 in its vertical position,
- the means 4 for emitting the light beam 5 in the direction of the cell 1, and
- the means 6 for receiving a backscattered light beam, comprising the matrix sensor 20,
- the optical conjugation means 17.

The analysis means 7 may be in the form of management electronics fixed to the support or arranged in a housing connected thereto.

According to the example represented in FIG. 1, the device advantageously comprises means for extending the light beam 5 emitted in the direction of the cell 1, in order to extend said beam in the vertical plane PV covering at least the height hc of the cell 1 containing the polyphase mixture 2, so that the light beam 5 is divergent in the vertical plane PV at its interface 9 between the inner surface 10 of the wall 18 of the cell 1 and the polyphase mixture 2. Still according to FIG. 1, these extension means are obtained by virtue of means 4, for emitting the light beam 5 in the direction of the cell 1, which comprise means 30 for generating at least one divergent light beam 31. The generator means 30 may, for example, consist of a generator of a vertical line of laser light diverging at the source in a vertical plane.

The optical conjugation means 17 allow one and only one point of the matrix sensor 20 to be made to correspond with each point of the scattering pattern on the surface of the mixture 2 analyzed. Measuring the light flux arriving on the matrix sensor 20 will thus be equivalent to measuring the surface flux density at each point of the scattering pattern. According to one property of the backscattered light, at each point of the wall-mixture interface the backscattered light is emitted with an equal intensity in all directions. The Applicant has thus observed that the intensity on the sensor corresponds to that emitted by the product even if the collection optics are placed so that they receive the light from each point of the surface of the mixture at different angles.

Figure 7:
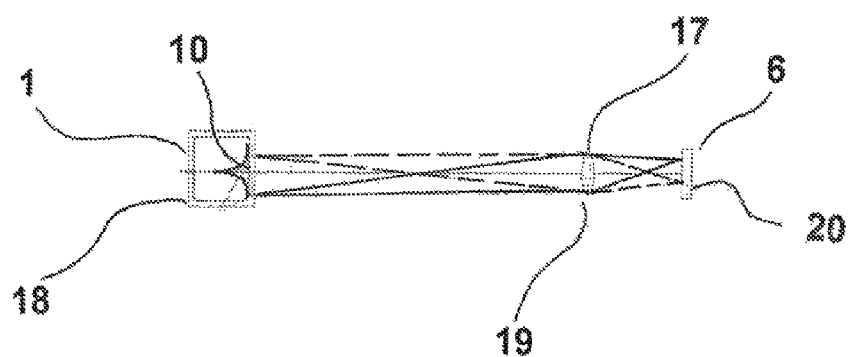
FIG. 7 represents a view from above of FIG. 6 with a different cell having a square cross section.

The optical conjugation means 17, as represented in FIG. 1, 5, 6 or 7, advantageously comprise means for collecting and focusing a part of the backscattered light beam, such as a simple biconvex lens 19 as represented in the figures, or of an optically equivalent type, for example a doublet or a triplet, or the like. The part of the backscattered light beam 3 collected by the optical conjugation means 17 furthermore extends in the horizontal direction, as represented in FIGS. 1 and 7, so as to collect information about the backscattered light on both sides of the vertical line of light incident on the cell 1, for example over the entire illuminated wall in the case of a cell 1 with a cross section which is polygonal, in particular square or rectangular as represented in FIG. 7, or over a part, shaped as an arc of a cylinder, of the cell 1 with a circular cross section, for which the incident vertical line of light lies in a substantially median position, as represented in FIG. 1.

The optical conjugation means 17, arranged between the cell 1 and the means 6 for receiving the light beam 3 backscattered by the polyphase mixture 2, are advantageously arranged so that the height hr of the receiver means is less than the height hc of the cell 1 capable of containing the polyphase mixture 2, as represented in the figures.

The optical conjugation means 17 are preferably placed at a height substantially equal to half the height of the cell 1, i.e. hc/2, in order to be equidistant between top and bottom interfaces of the illuminated mixture 2 when it completely fills the cell (not shown in the figures). Furthermore, the plane of the biconvex lens 19 or the like is preferably placed parallel to the interface 9 illuminated by the emitter means 4, which lies between the mixture 2 and the inner surface 10 of the wall 18 of the cell 1 in contact with said mixture. The biconvex lens 19 is defined by its magnification, and arranged between the matrix sensor and the cell 1, so that the image of the backscattered light extending over the mixture height is transmitted to the matrix sensor 20 and corresponds to the selected height of said sensor, as shown in FIG. 5. A similar principle is applied for the selected width of the matrix sensor 20, i.e. in order to conjugate the cell 1 with the size of the matrix sensor 20 while taking into account the cell width over which it is desired to obtain information relating to the backscattered light. FIG. 1 shows this conjugation in perspective. FIGS. 6 and 7 show the one-to-one relations in a vertical plane and in a horizontal plane between two points of the mixture 2, of which it is desired to obtain information by the light which is backscattered from these points, and two points of the matrix sensor 20.

As represented in FIG. 7, the optical conjugation means 17 and the matrix sensor 20 may advantageously be placed symmetrically with respect to a vertical plane which is perpendicular to the wall 18 of the cell 1, onto which the incident light beam is projected, and which comprises the line of light, or with respect to a plane intersecting with the plane defined above along the line of light and forming an angle with this plane defined above.

FIGS. 1 and 5 represent the optical field 21 by lines which connect the upper and lower ends of the cell 1 respectively to the lower and upper ends of the matrix sensor 20, the optical field being defined by the arrangement of the optical conjugation means 17, as a function of the ratio which is desired between the height of the cell 1 and that of the matrix sensor 20, and also as a function of the distance separating the cell from the matrix sensor 20.

Figure 2:
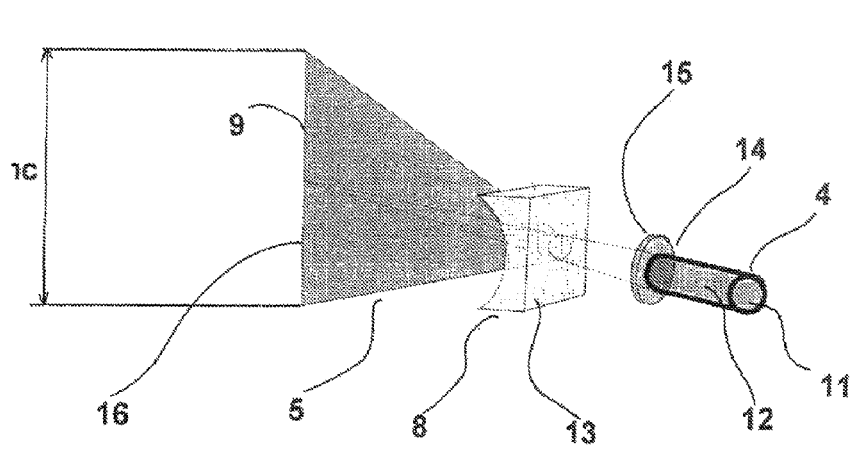
FIG. 2 represents a schematic perspective view of a second exemplary embodiment of a device according to the invention, which is partial and concerns the means for emitting a light beam in the direction of the cell.

FIGS. 2 to 4 show a second embodiment of the generation of the light beam 5 emitted in the direction of the cell 1, comprising means for extending the beam in the vertical plane. In this alternative embodiment, which differs from the first embodiment by a different implementation of the means for emitting the light beam 5 in the direction of the cell 1, the device according to the invention advantageously comprises means 14 for focusing the light beam 5 emitted in the direction of the cell 1, in order to focus this light beam 5, taken in a horizontal cross section SH, at its interface 9 between the inner surface 10 of the wall 18 of the cell 1 and the polyphase mixture 2.

In these FIGS. 2 to 4, the means 4 for emitting the light beam 5 in the direction of the cell 1 advantageously comprise:
the means 11 for generating a light beam 12, all the light rays of which are mutually parallel, which is referred to as a collimated light beam 12, for example a collimated laser source,
the means 8 for extending the light beam 5 emitted in the direction of the cell 1 being interposed between the means 11 for generating the collimated light beam 12 and the cell 1, and the focusing means 14 being arranged between the means 11 for generating the beam of collimated light 12 and the means 8 for extending the light beam 5 in the vertical plane PV.

The means 8 for extending the light beam 5 emitted in the direction of the cell 1 comprise, for example, divergent lens means on a (cylindrical) axis, for example a vertically divergent concave cylindrical lens 13.

The focusing means 14 make it possible to obtain according to the invention a light beam 5 emitted in the direction of the cell, at its interface 9 between the inner surface 10 of the wall 18 of the cell 1 and the polyphase mixture 2, which has a vertical line shape 16 whose width is less, preferably very much less, than the free transport path l* of the polyphase mixture 2, as will be detailed below with the description of the analysis means 7. These focusing means 14, in the example of FIGS. 2 to 4, consist of convergent lens means 15, for example an at least horizontally convergent cylindrical lens: in the example represented in these figures, a biconvex lens focusing the beam emitted by the generator means 11 toward a point. As represented in FIGS. 2 to 4, the focused beam 5 then passes through the vertically divergent concave cylindrical lens 13 which diverges the beam 5 in the vertical plane before reaching the cell, without modifying the convergence of the beam 5 given by the lens 15 in the horizontal plane, as shown in FIG. 3. The arrangement of the focusing means 14 makes it possible to offer the device according to the invention a light beam thinness which can advantageously be modified, for example by adjusting the position of the lens or the emitting source with respect to the cell.

FIGS. 8 to 10 show a third embodiment of the generation of a light beam 5 emitted in the direction of the cell 1, comprising means for extending the beam in the vertical plane in the manner of the first and second embodiments. In this third embodiment, the means 30 for generating a divergent light beam 31 comprise a bare laser source 30 producing an initial light beam which is divergent in the horizontal and vertical planes. This initial light beam is focused in a horizontal plane by focusing means 14 consisting, for example, of a horizontally convergent cylindrical lens as represented in FIGS. 8 and 9.

FIGS. 11 to 13 show a fourth embodiment of the generation of a light beam 5 emitted in the direction of the cell 1, comprising means for extending the beam in the vertical plane in the manner of the other embodiments. In this fourth embodiment, the means 30 for generating a divergent light beam 31 comprise a linear light source 41 comprising plurality of juxtaposed divergent point light sources 42 producing an initial light beam which is divergent in the horizontal and vertical planes. This initial light beam is focused in a horizontal plane by focusing means 14 consisting, for example, of a convergent conjugation lens as represented in FIGS. 11 to 13.

Several embodiments of the means for emitting the light beam 5 emitted toward the cell 1 have been described above. However, any means for projecting a line of light may be used, for example the projection of a line-shaped mask of the photographic slide type. It is not necessary to use a coherent light source, such as a laser is. A laser is advantageous because it makes it possible to obtain a thin light beam having a high light intensity relatively easily.

The line of light 16 may have a width which gives it the shape of an elongate rectangle. A rectangle has the benefit of optically averaging a possible irregularity of the mixture itself. In order to analyze the stability of products in relation to gravity, this shape may consist of merely stretching an arbitrary profile along the vertical axis. The wavelength of the light may be selected as a function, for example, of the spectral absorption of the product. Specifically, it is often advantageous to work with a wavelength for which the product has little absorption. For example, the near infrared range for petroleum products. Each light point of this line of light 16 will be spread to a greater or lesser extent horizontally as a function of the local scattering properties of the product. Thus, the almost ideal line of light 16 will be deformed, and widened to a greater or lesser extent. This deformation along the height, picked up by the matrix sensor 20 via the optical conjugation means 17, will provide information about the variations in scattering properties of the product along the height.

The matrix sensor 20 may be provided by a 2D matrix of the CCD or CMOS type. A distance between the matrix sensor 20 and the cell 1 immediately leads to a great loss of spatial resolution of the measurement. This is because the backscattered light essentially consists of rays which are distributed in all directions and a distance from the sensor thus leads to a strong blurring effect. In order to have correct signal capture without these conjugation optics, it would be necessary to place the sensor against the flask, which of course interferes with the injection of light. The sensor could be transparent, which is possible, but not standard and would therefore entail a very large extra cost. It is possible to use a very inexpensive video sensor. The flexible nature (modifiable thinness of the incident line of light, adaptable imaging focal length, various choices of the camera resolution) allows the device according to the invention to be adapted readily to a given family of chemical products and allows a range of instruments to be designed easily for these families, for example for highly scattering products (high resolution). The device according to the invention therefore allows good market satisfaction. The measurement may be carried out through a window, which makes it possible to put the cell containing the mixture to be analyzed in a chamber of moderate volume (of the order of 1 dm$^3$). This small volume allows easy implementation of thermal and/or humidity level regulation or the like.

The means 7 for analyzing the part of the light beam 3 backscattered by the polyphase mixture 2 and received by the matrix sensor 6 via the optical conjugation means 17 will now be described with the aid of FIGS. 14 to 15.

FIGS. 14 to 22 show examples of a mixture analyzed with a device as described above.

Several algorithms may be used in order to process the image obtained on the matrix sensor 20. For example, as represented in FIGS. 14 and 15, the pixels of a horizontal line of the matrix sensor 20 may be selected, corresponding to a given height h1, h2, etc. . . . on the cell 1. A curve is thus obtained (FIG. 15) of light intensity (on the ordinate) as a function of the transverse coordinate (on the abscissa) for each height h1, h2, etc. This curve is referred to as a "transverse profile".

Advantageous processing operations may be those which for each measurement, i.e. an illumination over the height of the mixture analyzed at a time t, give a curve as a function of the vertical coordinate (height). In order to do this, it is necessary to convert each "transverse profile" into a simple number representative of the scattering properties of the product analyzed.

A first example of "transverse profile" processing would simply be the value of the light intensity at the center of the profile.

Another example would be to measure the width of the "transverse profile". For example the width at half height of each curve on FIG. 15, or alternatively the width of a Gaussian curve fitted to the profile, or else a statistical width: $LX=[\int I(x)x^2 dx/(x)dx]^{1/2}$ with $I(x)$ representing the light intensity of the profile for the transverse coordinate x (with the origin at the center of the profile).

It is known that the light intensity of a point P separated by a distance r from a point light source S obeys the following law:

$$I(r)=I_0/r^3,$$

with $I_0$ representing the light intensity at the point source S.

The Applicant has observed that illuminating the analyzed medium along a line of light causes, in backscattering, perturbations of the backscattered light picked up by the receiver means, consisting of the light backscattered by a determined point of the illuminated mixture being merged with the light simultaneously backscattered by the adjacent points above and below the point in question. These perturbations modify the nature of the backscattered signal picked up, and it is therefore advantageous to provide specific means for analysis over the height of the illuminated cell, which take these perturbations into account.

The Applicant has observed that in the absence of absorption, the light intensity of a point P separated by a distance x, for x>>l*, of a line of light L does not obey the law above but satisfies a different law as below:

$$I(x)=2I_0/x^2,$$

the decrease being proportional to the square of the distance to the source, with $I_0$ representing the light intensity at the point source L.

Another example would be to give the integral of the light intensity of these "transverse profiles", as represented in FIG. 15 as a hatched region. This gives a good overall signature of the variations in the scattering properties of the product as a function of height. The advantage of this processing over the first (only the height at the center) is that at the same time it takes an average along the transverse axis, which greatly reduces the measurement noise.

It is possible to apply more sophisticated processing operations, for example empirical or theoretical modeling of the shape of the transverse profile, which comprises the transport length parameter denoted l* or alternatively the absorption length parameter denoted $l_a$:$I(x)=f(l^*,l_a,x)$. Thus, fitting of this theoretical profile to each "transverse profile" obtained by one of the devices described above may be carried out, so as to obtain a series of numbers l* and optionally $l_a$ for each vertical coordinate.

By virtue of the combination of injecting a narrow line of light onto the product analyzed, the width of which is advantageously less than l* and furthermore the $l_a$ of the product analyzed, the device according to the invention, several exemplary embodiments of which have been described above, makes it possible to give a measurement both of the absorption (length $l_a$) and of the scattering (length l*).

It should be recalled that l* is the equivalent mean free path for isotropic scattering, or in other words the distance beyond which the photon which enters the product has completely lost its initial direction. l* is the standard physical parameter for characterizing the scattering properties of the product. If l*, the concentration and the optical indices are known, it is for example possible to calculate the diameter of the particles by methods known to the person skilled in the art. Let us also recall that $l_a$ is the length of the path of the photon before being absorbed; its value is infinite for white products and tends toward zero for dark products.

It is thus preferable to use a very thin line of light (width<<l*) in order to have a profile shape which genuinely depends on the scattering properties of the product and not on the profile of the line of light itself.

By virtue of the distance of a few centimeters between the emitter means 4 and the receiver means 6 as a group on the one hand, and the cell 1 on the other hand, it is readily possible to construct a device which analyzes the stability of a plurality of samples at once with a single optical head. An optical head is intended to mean a part of the analysis device comprising the emitter means 4, the receiver means 6, and the optical conjugation means 17. For example, a kind of carousel may be envisaged which makes it possible to accommodate a plurality of cells, or alternatively a row of cells on a straight support (these are not shown). In the "multi-receptacle" configuration example using a kind of carousel, the optical head rotates at the center of the carousel so as to successively measure each cell or flask of product or mixture to be analyzed. Possible misalignments due to mechanical defects of the rotating system may perfectly well be corrected by software. In the "multi-receptacle" configuration example using a linear cell support, either the optical head moves or the cell support moves, in translation with respect to one another, so as to successively measure each cell of product.

Figure 18:
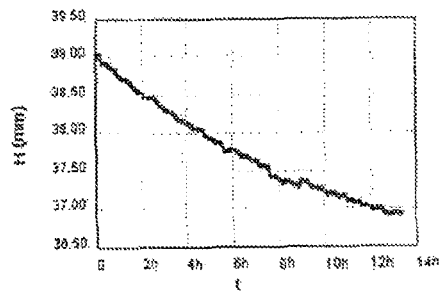

FIGS. 16, 17 and 18 represent a first example of use of a device according to the invention as described above, for studying the sedimentation of a suspension of titanium dioxide ($TiO_2$) in water. The experiment carried out is as follows: the suspension has a volume fraction of 3.8%. The average size of the titanium dioxide particles is 2 micrometers. The suspension is placed in a cylindrical receptacle with a diameter of 28 mm and a height of 50 mm, having a transparent wall. The suspension is first homogenized then placed in an analysis device according to the invention. A measurement over the entire height in backscattering is carried out every 10 minutes for 13 hours. FIG. 17 represents a series of curves which are obtained after having used the processing which gives the value of the area under the "transverse profiles" on the ordinate for each cell height defined on the abscissa, as described above.

FIG. 16 represents the appearance of an image of the scattering pattern. This is a raw image. On the curves in FIG. 17, a variation of the straight part of the profile can be seen (top part of the suspension), which clearly indicates progressive descent of the sedimentation front.

For example, the sedimentation rate may be given by plotting the height of the sedimentation front as a function of time, as represented in FIG. 18 on which the slope of the curve corresponds to the sedimentation rate. Here, for example, it is found that the sedimentation rate is 184.6 micrometers per hour on average.

Figure 19:
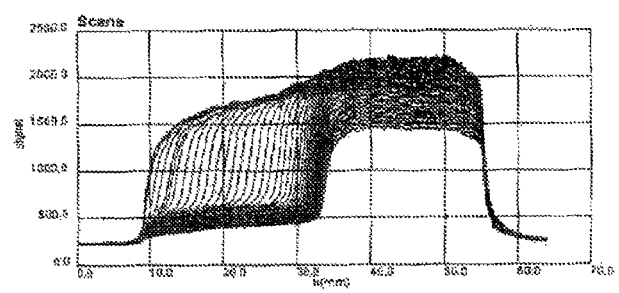
FIGS. 19 and 20 relate to a second example of use of a device according to the invention, for studying the creaming of an emulsion.
Figure 20:
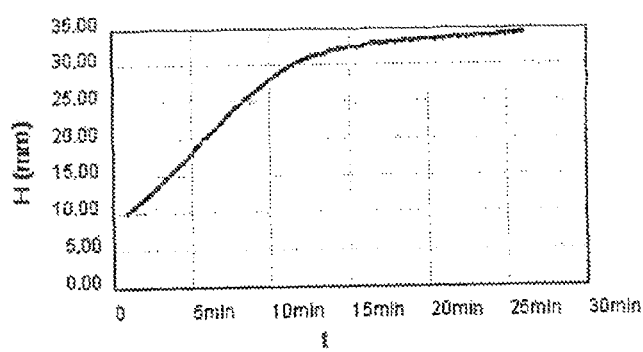

FIGS. 19 and 20 represent a second example of use of a device according to the invention as described above, relating to an example of measuring the creaming of an emulsion over 26 minutes by using the "integral under the profile" processing described above. The drops of oil, which are less dense than water, rise to the surface. FIG. 19 shows a series of curves which are obtained after having used the processing which gives the value of the area under the "transverse profiles" on the ordinate for each height defined on the abscissa. FIG. 20 shows the height of the creaming front (on the ordinate) as a function of time (on the abscissa). The slope of the curve represents the creaming rate.

Figure 21:
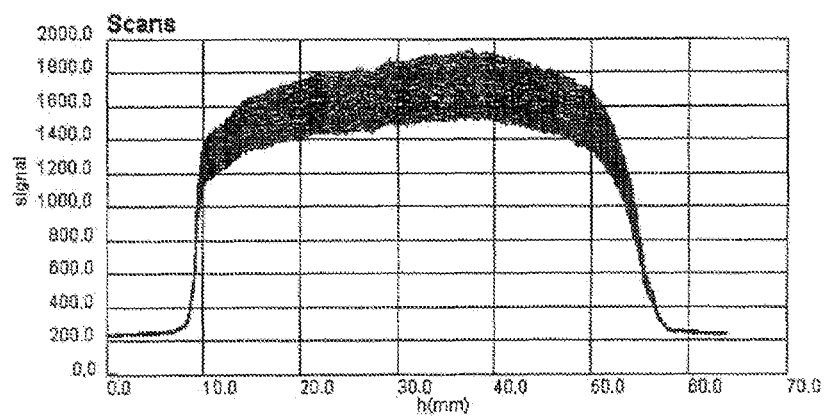
FIGS. 21 and 22 relate to a third example of use of a device according to the invention, for studying the coalescence of an emulsion.
Figure 22:
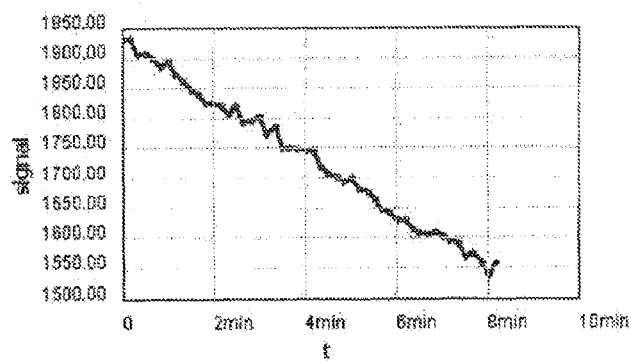

FIGS. 21 and 22 represent a third example of use of a device according to the invention as described above, relating to an example of measuring the coalescence of an emulsion over 8 minutes by using the "integral under the profile" processing described above. The drops of oil combine to form larger drops. The size variation modifies the height of the signal. There is no particle migration, so the signal remains uniform. FIG. 21 shows a series of curves which are obtained for coalescence of drops. FIG. 22 represents the kinetics showing the drop in the signal.

The invention claimed is:

1. A device for analyzing a polyphase mixture (2) via a light beam (3) backscattered by said mixture, comprising:
   a cell (1) having a capacity component of vertical extent, capable of containing the polyphase mixture,
   means (4) for emitting a light beam (5) in a direction of the cell, so that the light beam extends in a vertical plane (PV) covering at least a height (hc) of the cell containing the polyphase mixture (2),
   means (6) for receiving at least a part of the light beam (3) backscattered by said polyphase mixture, covering a backscattered light beam (3) height extending over the height (hc) of the cell containing the polyphase mixture (2), characterized in that the device further comprises:
   optical conjugation means (17) arranged between the cell (1) and the means (6) for receiving at least a part of the light beam (3) backscattered by the polyphase mixture (2),
   said receiver means (6) comprising a matrix sensor (20) provided with a plurality of pixels, forming a surface for receiving said at least part of the backscattered light beam, extending along a vertical direction and a horizontal direction,
   means (7) for analyzing said at least part of the light beam (3) backscattered by the polyphase mixture (2) and received by the matrix sensor (20) via the optical conjugation means (17),
   the light beam (5) emitted in the direction of the cell having, at an interface (9) between an inner surface (10) of a wall (18) of the cell (1) and the polyphase mixture (2), a vertical line shape (16) whose width is less, than a free transport path (1*) of the polyphase mixture (2).

2. The device as claimed in claim 1, wherein the cell capable of containing said polyphase mixture has a vertical right cylindrical shape.

3. The device as claimed in claim 1, further comprising means (8) for extending the light beam emitted in the direction of the cell (1), in order to extend said beam in a vertical plane (PV) covering at least the height (hc) of the cell capable of containing said polyphase mixture (2), so that the light beam is divergent in said vertical plane (PV) at the interface (9) between the inner surface (10) of the wall (18) of the cell (1) and the polyphase mixture (2).

4. The device as claimed in claim 1, further comprising means (14) for focusing the light beam (5) emitted in the direction of the cell (1), taken in a horizontal cross section (SH), at the interface (9) between the inner surface (10) of the wall (18) of the cell (1) and the polyphase mixture (2).

5. The device as claimed in claim 1, wherein the optical conjugation means (17), arranged between the cell (1) and the means (6) for receiving the light beam (3) backscattered by the polyphase mixture (2), are arranged so that height (hr) of the receiver means is less than height (hc) of the cell capable of containing said polyphase mixture.

6. The device as claimed in claim 1, wherein the optical conjugation means (17) is a biconvex lens for collecting and focusing said at least part of the backscattered light beam.

7. The device as claimed in claim 2, wherein the cell of vertical right cylindrical shape has a circular cross section.

8. The device as claimed in claim 3, wherein said means (4) for emitting the light beam (5) in the direction of the cell (1) comprise:

means (11) for generating a collimated light beam (12), all the light rays of which are mutually parallel, said means (8) for extending the light beam (5) emitted in the direction of the cell (1) being interposed between said means (11) for generating a collimated light beam (12) and the cell (1).

9. The device as claimed in claim 3, wherein said means (8) for extending the light beam (5) emitted in the direction of the cell (1) comprise vertically divergent concave cylindrical lens means (13).

10. The device as claimed in claim 3, wherein said means (4) for emitting the light beam (5) in the direction of the cell (1) comprise means (30) for generating at least one divergent light beam (31).

11. The device as claimed in claim 4, wherein said focusing means (14) are arranged between the means (11) for generating the beam of collimated light (12) and the means (8) for extending the light beam (5) in the vertical plane (PV).

12. The device as claimed in claim 4, wherein said focusing means (14) comprise convergent lens means (15).

13. The device as claimed in claim 12, wherein said focusing means (14) comprise horizontally convergent cylindrical lens means.

14. The device as claimed in claim 10, wherein said means (30) for generating at least one divergent light beam (31) comprise a linear light source (41).

15. The device as claimed in claim 14, wherein said linear light source (41) comprises a plurality of divergent point light sources (42).

16. The device as claimed in claim 5, further comprising means (14) for focusing the light beam (5) emitted in the direction of the cell (1), taken in a horizontal cross section (SH), at the interface (9) between the inner surface (10) of the wall (18) of the cell (1) and the polyphase mixture (2).

17. The device as claimed in claim 5, further comprising means (8) for extending the light beam emitted in the direction of the cell (1), in order to extend said beam in a vertical plane (PV) covering at least the height (hc) of the cell capable of containing said polyphase mixture (2), so that the light beam is divergent in said vertical plane (PV) at the interface (9) between the inner surface (10) of the wall (18) of the cell (1) and the polyphase mixture (2).

18. The device as claimed in claim 6, wherein the optical conjugation means (17), arranged between the cell (1) and the means (6) for receiving the light beam (3) backscattered by the polyphase mixture (2), are arranged so that the height (hr) of the receiver means is less than height (hc) of the cell capable of containing said polyphase mixture.

19. The device as claimed in claim 6, further comprising means (14) for focusing the light beam (5) emitted in the direction of the cell (1), taken in a horizontal cross section (SH), at the interface (9) between the inner surface (10) of the wall (18) of the cell (1) and the polyphase mixture (2).

20. The device as claimed in claim 6, further comprising means (8) for extending the light beam emitted in the direction of the cell (1), in order to extend said beam in a vertical plane (PV) covering at least the height (hc) of the cell capable of containing said polyphase mixture (2), so that the light beam is divergent in said vertical plane (PV) at the interface (9) between the inner surface (10) of the wall (18) of the cell (1) and the polyphase mixture (2).

\* \* \* \* \*